United States Patent
Liu et al.

(10) Patent No.: US 9,869,868 B2
(45) Date of Patent: Jan. 16, 2018

(54) LIGHT SPLITTING MODULE FOR OBTAINING SPECTRUMS AND DUAL-MODE MULTIPLEXING OPTICAL DEVICE

(71) Applicant: University of Electronic Science and Technology of China, Chengdu, Sichuan (CN)

(72) Inventors: Ziji Liu, Sichuan (CN); Xuan He, Sichuan (CN); Xing Xiong, Sichuan (CN); Zhiqing Liang, Sichuan (CN); Yadong Jiang, Sichuan (CN)

(73) Assignee: University of Electronic Science and Technology of China, Chengdu, Sichuan (CN)

( * ) Notice: Subject to any disclaimer, the term of this patent is extended or adjusted under 35 U.S.C. 154(b) by 0 days.

(21) Appl. No.: 15/625,429

(22) Filed: Jun. 16, 2017

(65) Prior Publication Data
US 2017/0285353 A1    Oct. 5, 2017

(30) Foreign Application Priority Data

Jun. 16, 2016  (CN) .......................... 2016 1 0431962

(51) Int. Cl.
*G01N 21/25*      (2006.01)
*G02B 27/10*     (2006.01)
*G02B 5/20*       (2006.01)
*G02B 3/00*       (2006.01)

(52) U.S. Cl.
CPC ....... *G02B 27/1013* (2013.01); *G01N 21/255* (2013.01); *G02B 3/0056* (2013.01); *G02B 5/201* (2013.01)

(58) Field of Classification Search
CPC .......... G01N 21/25; G02B 27/10; G02B 5/20; G02B 3/00; G01J 3/28; G01J 3/46; G01J 3/02; G01J 3/51
See application file for complete search history.

(56) References Cited

U.S. PATENT DOCUMENTS

2015/0233762 A1*  8/2015  Goldring ................ G01J 3/108
                                                                356/451

* cited by examiner

*Primary Examiner* — Abdullahi Nur

(57) ABSTRACT

A light splitting module for obtaining spectrums of an object to be tested is disclosed, which sequentially includes a light entrance window, a diffuser and a filter array along a light entrance direction, wherein the filter array is an angle modulated filter array which has multiple subareas and includes multiple filters with different center wavelengths respectively corresponding to the subareas. Also, a dual-mode multiplexing optical device is disclosed, which includes the light splitting module, an illumination module and a light field imaging module, can realize the integration of spectral detection and light field imaging, so it can be applied to material spectral detection, digital image detection and digital focusing for obtaining high-resolution imaging results; and simultaneously, the modules of the device are detachable, so that users can use the device as required.

10 Claims, 3 Drawing Sheets

LIGHT SPLITTING MODULE FOR OBTAINING SPECTRUMS AND DUAL-MODE MULTIPLEXING OPTICAL DEVICE

CROSS REFERENCE OF RELATED APPLICATION

The present invention claims priority under 35 U.S.C. 119(a-d) to CN 201610431962.1, filed Jun. 16, 2016.

BACKGROUND OF THE PRESENT INVENTION

Field of Invention

The present invention relates to a technical field of optical imaging, and more particularly to a light splitting module for obtaining spectrums and a dual-mode multiplexing optical device comprising the light splitting module.

Description of Related Arts

The light field is a parameterized representation of the four-dimensional optical radiation field in the space that contains both the two-dimensional position (x, y) and the two-dimensional direction information (u, v). With the development of photographic technology, the light field imaging technology is widely used in three-dimensional reconstruction, digital focusing and so on. Compared with conventional imaging methods, the light field imaging technology can obtain richer target information (including the perceived direction information of emitted lights besides the target location information), so that in the image reconstruction or processing, these extra information can solve many problems existing in the conventional technology such as image defocusing, multi-object focusing and motion blur, thus the light field imaging technology is applied to aerial photography, animation rendering, stereo projection, instrument measurement and so on.

The spectral detection technology can help users to understand the material composition and structure, and is a necessary analysis means, so different types of spectrometers, such as raster scanning spectrometers and Fourier transform spectrometers, are developed based on the spectral detection technology. Conventional spectrometers rely on a large number of optical components, and are often bulky and costly. In order to follow the development tendency of miniaturization and low cost, a new spectral detection method is to be proposed.

SUMMARY OF THE PRESENT INVENTION

An object of the present invention is to provide a light splitting module for obtaining spectrums and a dual-mode multiplexing optical device comprising the light splitting module, so as to solve deficiencies of above-mentioned prior arts.

To achieve the above object, the present invention adopts technical solutions as follows.

A light splitting module for obtaining spectrums of an object to be tested, sequentially comprises a light entrance window, a diffuser and a filter array along a light entrance direction, wherein a size of the filter array is $D_x \times D_y$, maximum divergent angles of the diffuser along a horizontal direction and a vertical direction thereof are respectively $\theta_x$ and $\theta_y$, a distance d between the filter array and the diffuser meets $$0 < d \leq \min\left\{\frac{D_x}{2}\cot\theta_x, \frac{D_y}{2}\cot\theta_y\right\},$$

the light entrance window is made from materials which is transparent at specific bands, the specific bands are target bands of the light splitting module, the filter array is an angle modulated filter array which has multiple subareas and comprises multiple filters with different center wavelengths respectively corresponding to the subareas, a maximum divergent angle of the diffuser is $\theta_{max}=\max\{\theta_x, \theta_y\}$, and a maximum adjustable angle $\alpha$ of the filters of the filter array meets $\alpha \leq \theta_{max}$.

Also, the present invention provides a dual-mode multiplexing optical device comprising the above-mentioned light splitting module, further comprises:

an illumination module adapted for providing an object to be tested with illumination; and a light field imaging module, adapted for achieving light field imaging of the object to be tested, sequentially comprises a convergent lens, a microlens array, a detector and a first control circuit along a light entrance direction, wherein: the convergent lens converges lights from the filter array on a plane of microlenses of the microlens array, the microlens array projects lights from the filters corresponding to the microlenses on the detector in a form of spectrums, the detector detects the spectrums or light field imaging results of the object to be tested, the first control circuit controls the detector to shoot the spectrums and the light field imaging results, wherein: the illumination module and the light splitting module form a whole, the illumination module is placed at one side of the light entrance window of the light splitting module, the light splitting module is in detachable connection with the light field imaging module.

Furthermore, an angle between emergent lights of the illumination module and the light entrance window is adjustable for ensuring that reflected lights and scattered lights of the object are vertically incident to the light entrance window as far as possible.

Preferably, a surface of the diffuser is coated with a layer of antireflective film, and/or the surface of the diffuser has a surface profile in a form of the microlens array.

Preferably, the filters of the filter array are Fabry-Perot filters, film filters or interference filters.

Preferably, the illumination module further comprises a second control circuit for controlling lightening the illumination module and adjusting brightness of the illumination module.

Preferably, the microlenses of the microlens array are respectively corresponding to the filters of the filter array; a projection of each microlens on the filter array is completely located in an area covered by a single filter corresponding to the microlens; the microlens array is located on a focal plane of the convergent lens; the detector is located on a focal plane of the microlens array; a focal length of each microlens is the same; a gap $\delta$ is provided between adjacent microlenses of the microlens array and is coated with a light-absorbing film, a relationship between the gap $\delta$ and a diameter $\sigma$ of defocused spots of the focal plane of the microlens array is $\delta \geq \sigma$; the light-absorbing film is adapted for reducing light interferences between the adjacent microlenses.

Preferably, every filter is square, a diameter of every microlens of the microlens array is smaller than or equal to an inscribed circle diameter of the square filter.

Preferably, all microlenses are aspherical for reducing aberrations.

Preferably, the convergent lens is placed at a forefront of the light field imaging module and is at least one member selected from a group consisting of plano-convex lens, biconvex lens and aspherical lens.

Preferably, an interlayer support structure is located between the microlens array and the detector, and a length of the interlayer support structure is equal to the focal length of the microlens array.

Beneficially effects of the present invention are as follows. Instead of traditional grating interferometers, Michelson interferometer and other light splitting methods, the present invention proposes a light splitting module based on an angle modulated filter array and a dual-mode multiplexing optical device comprising the above-mentioned light splitting module which utilizes the light field imaging technology. The light splitting module is adapted for obtaining spectrums of the object to be tested; after lights are incident on the angle modulated filter array, the spectrums on a regular distribution related to the wavelength and the emergent angle are obtained. When the light field imaging technology is applied to spectral detection, due to the effective perception of changes in light angles, spectral detection results have a high resolution to achieve the function of the spectrometer. In addition, the angle modulated filter array is simple in manufacturing process and low in cost, and can be processed into any shape and size, so as to create more possibilities for device miniaturization. The dual-mode multiplexing optical device, provided by the present invention, can realize the integration of spectral detection and light field imaging, so it can be applied to material spectral detection, digital image detection and digital focusing for obtaining high-resolution imaging results; and simultaneously, the modules of the device are detachable, so that users can use the device as required.

Figure 1:
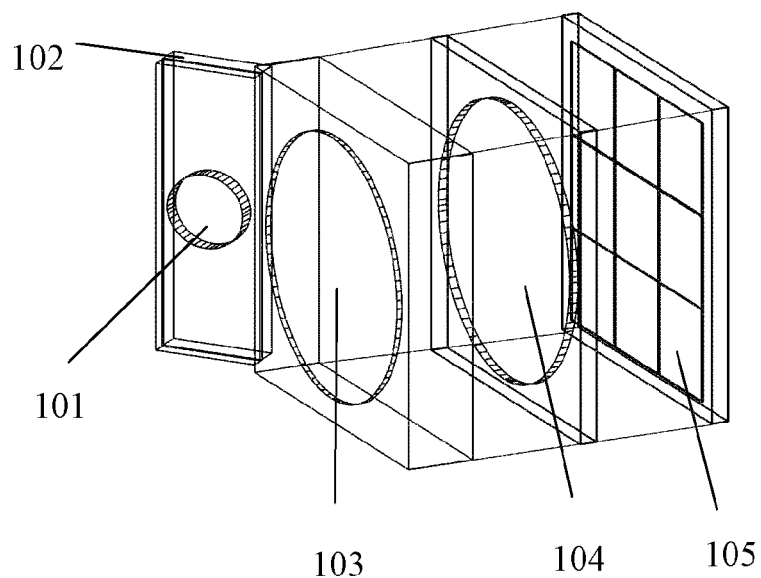
FIG. 1 is a structurally schematic view of an illumination module and a light splitting module of the present invention.

In the drawings, 101: light source of illumination module; 102: second control circuit; 103: light entrance window; 104: diffuser; 105: filter array; 106: convergent lens; 107: microlens array; 108: detector; 109: first control circuit; 1, 2 and 3: filter.

Furthermore, δ indicates a gap between adjacent microlenses; $\lambda_1$, $\lambda_2$ and $\lambda_3$ respectively indicate lights with different wavelengths.

DETAILED DESCRIPTION OF THE PREFERRED EMBODIMENT

Other advantages and effects of the present invention will become apparent to those skilled in the art from the following disclosure of the present invention by way of specific embodiments with reference to the accompanying drawings as follows. The present invention may also be embodied or applied by further different embodiments, and the details in this specification may be modified or varied without departing from the spirit of the present invention on the basis of different views and applications.

First Preferred Embodiment

Figure 4:
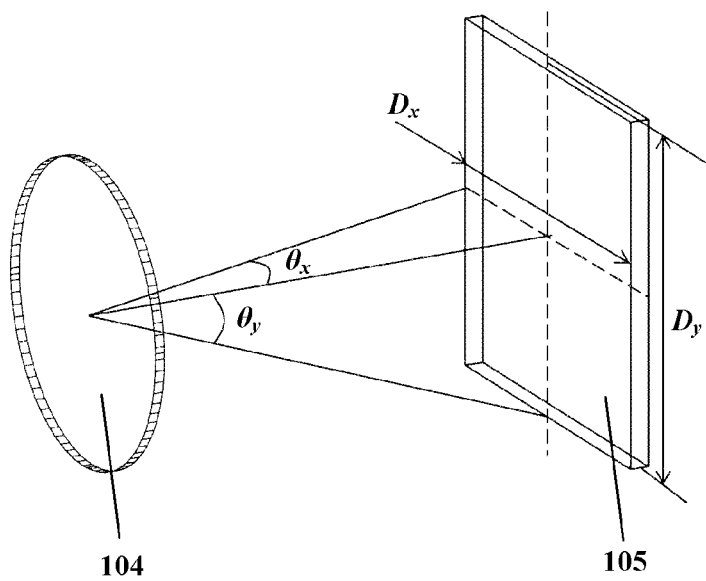
FIG. 4 is a structurally schematic view of a diffuser and a filter array of the present invention.

As shown in FIG. 1, a light splitting module for obtaining spectrums of an object to be tested is illustrated, which sequentially comprises a light entrance window 103, a diffuser 104 and a filter array 105 along a light entrance direction, wherein a size of the filter array is Dx×Dy. Referring to FIG. 4, maximum divergent angles of the diffuser along a horizontal direction and a vertical direction thereof are respectively $\theta_x$ and $\theta_y$; a distance d between the filter array and the diffuser meets $$0 < d \leq \min\left\{\frac{D_x}{2}\cot\theta_x, \frac{D_y}{2}\cot\theta_y\right\};$$

when the above-mentioned conditions are met, the device space is able to be effectively utilized; when are not, a partial area of the filter array is wasted. The light entrance window is made from materials which are transparent at specific bands, and the specific bands are target bands of the light splitting module. The filter array is an angle modulated filter array and has a series of subareas, and a filter is provided on every subarea, that is, the filter array comprises a series of filters. All filters respectively corresponding to all subareas of the filter array have different center wavelengths, a maximum divergent angle of the diffuser is $\theta_{max}=\max\{\theta_x, \theta_y\}$, and a maximum adjustable angle α of the filters of the filter array meets $\alpha \leq \theta_{max}$.

Second Preferred Embodiment

Figure 3:
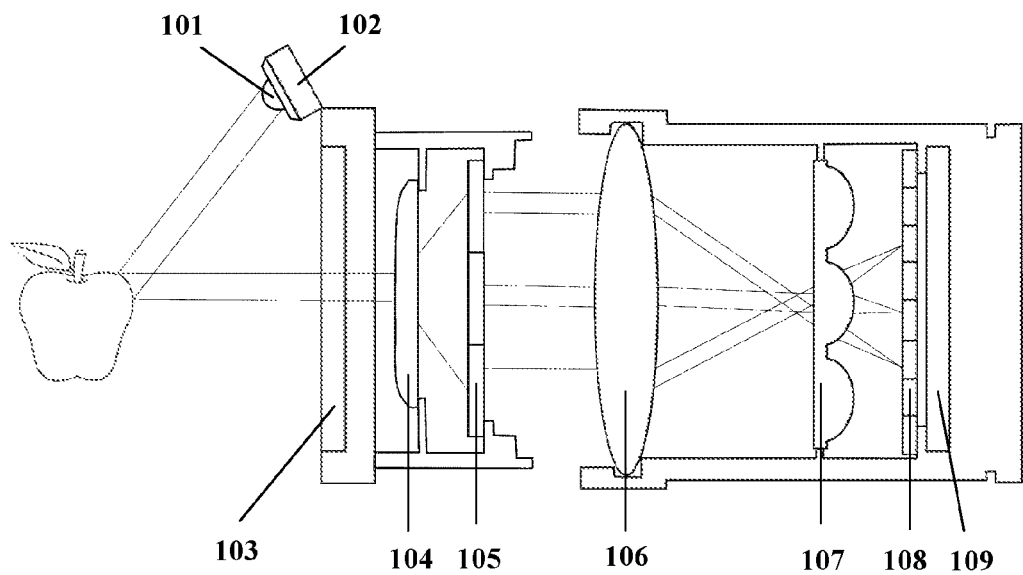
FIG. 3 is a structurally schematic view of a dual-mode multiplexing optical device of the present invention.

As shown in FIG. 3, a dual-mode multiplexing optical device comprises the light splitting module described according to the first preferred embodiment of the present invention. The dual-mode multiplexing optical device further comprises an illumination module adapted for providing an object to be tested with illumination, which comprises a light source 101; a light field imaging module, adapted for achieving light field imaging of the object to be tested, sequentially comprises a convergent lens 106, a microlens array 107, a detector 108 and a first control circuit 109 along a light entrance direction, wherein: the convergent lens converges lights from the filter array on a plane of microlenses of the microlens array, the microlens array projects lights from the filters corresponding to the microlenses on the detector in a form of spectrums, the detector detects the spectrums or light field imaging results of the object to be tested, the first control circuit controls the detector to shoot the spectrums and the light field imaging results; the illumination module and the light splitting module form a whole, the illumination module is placed at one side of the light entrance window of the light splitting module, the light splitting module is in detachable connection with the light field imaging module, such as threaded connection, spline connection and buckle connection.

The illumination module is able to be achieved through any current illumination devices, such as lasers, QLEDs (quantum dot light emitting diodes), infrared LEDs and halogen lamps. The illumination module is able to be achieved in a form of LED array. In some embodiments, all LEDs in the array are different in radiative spectrums, which causes that a total spectrum of the illumination module covers from a visible light band to a near-infrared light band. The illumination module further comprises a solar concentrating device for converging lights emitted by a light source to a sample to be tested.

The illumination module emits lights to the sample, and then lights reflected by the sample irradiate the diffuser through the light entrance window of the light splitting module.

Furthermore, an angle between emergent lights of the illumination module and the light entrance window is adjustable, for example, the illumination module is in hinged connection with one side of the light entrance window of the light splitting module, which ensures that reflected lights and scattered lights of the object are vertically incident to the light entrance window as far as possible. The illumination module further comprises a second control circuit 102 for controlling lightening the illumination module and adjusting brightness of the illumination module.

The detector is able to be any one of existing detectors, such as CCD or CMOS.

A surface of the diffuser is coated with a layer of antireflective film, and/or the surface of the diffuser has a surface profile in a form of the microlens array. Lights transmitted to the diffuser are homogenized through the diffuser 104, so that transmitted lights have a uniform spectral distribution. Therefore, the lights with various wavelengths have a basically same divergent angle range of 0-$\theta$°.

The filters of the filter array are Fabry-Perot filters, film filters or interference filters.

Figure 5:
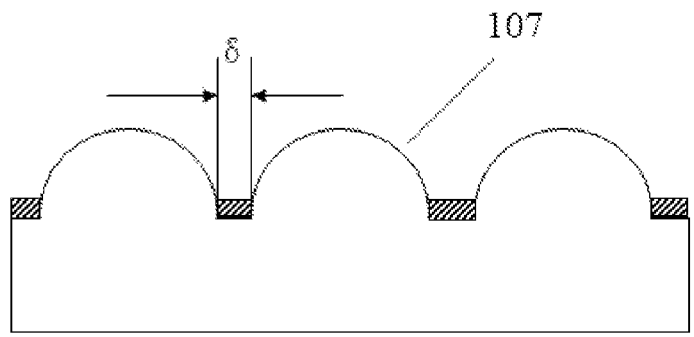
FIG. 5 shows that gaps of the microlens array are coated with a film.

The microlenses of the microlens array are respectively corresponding to the filters of the filter array; the projection of each microlens on the filter array is completely located in an area covered by a single filter corresponding to the microlens; the microlens array is located on a focal plane of the convergent lens; the detector is located on a focal plane of the microlens array; a focal length of each microlens is the same. As shown in FIG. 5, a gap $\delta$ is provided between adjacent microlenses of the microlens array and is coated with a light-absorbing film, a relationship between the gap $\delta$ and a diameter $\sigma$ of defocused spots of the focal plane of each microlens of the microlens array is $\delta \geq \sigma$. The light-absorbing film is adapted for reducing light interferences between the adjacent microlenses.

Each filter is square, a diameter of every microlens of the microlens array is smaller than or equal to an inscribed circle diameter of the square filter.

The microlenses are aspherical for reducing aberrations.

The convergent lens is placed at a forefront of the light field imaging module and is at least one member selected from a group consisting of plano-convex lens, biconvex lens and aspherical lens.

An interlayer support structure is located between the microlens array 107 and the detector 108, and a length of the interlayer support structure is equal to the focal length of the microlens array.

Figure 7:
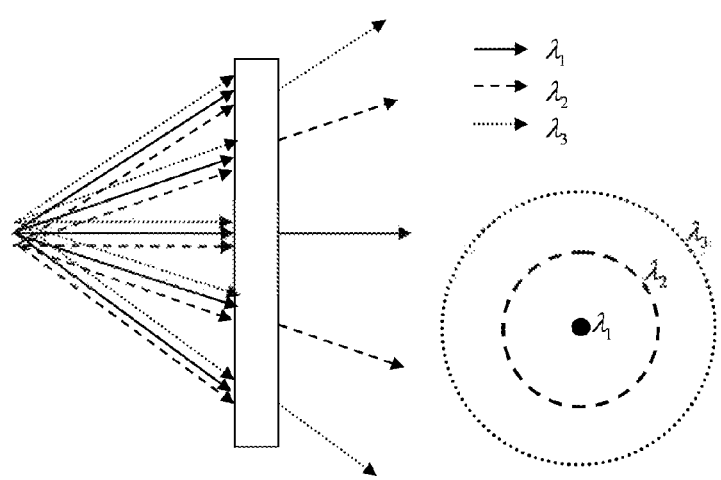
FIG. 7 is an emission spectrum distribution diagram of a filter.

Referring to FIG. 7, due to angle modulated characteristics of the filter array, there is a one-to-one relationship between a light emergent angle and an emergent light wavelength of any one filter of the filter array 105, the emergent lights have a regular spectral distribution which are shown in a form of multiple nested concentric rings. In some embodiments, the larger the radius of the ring is, the shorter the corresponding wavelength is.

Figure 6:
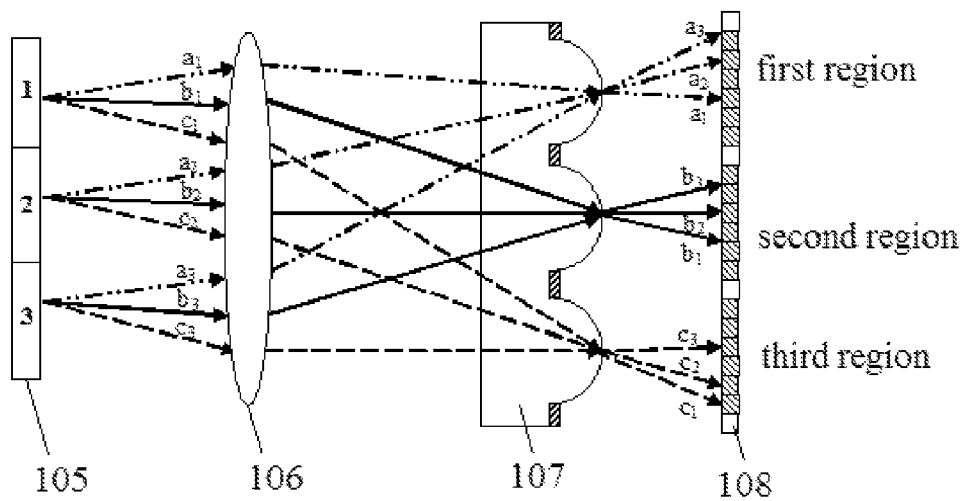
FIG. 6 shows light transmission of modules in optical field.

As shown in FIG. 6, ai, bi and ci (here, i=1, 2 and 3) respectively represent lights with three emergent angles (which are corresponding to three different wavelengths) of filters 1, 2 and 3 of the filter array 105, wherein a subscript i represents an $i^{th}$ filter, and a, b and c respectively represent three different emergent angles. Emitted lights from all the filters are converged by the convergent lens 106 to be focused on the microlens array which is placed at the focal plane of the convergent lens 106. Lights with different emergent angles are respectively corresponding to different microlenses, and are finally projected on different areas on the detector 108. In FIG. 6, spectral distributions of the three filters with the emergent angles of a, b and c are detected on a first region, a second region and a third region of the detector, and finally optical signals are converted into electrical signals.

Third Preferred Embodiment

Figure 2:
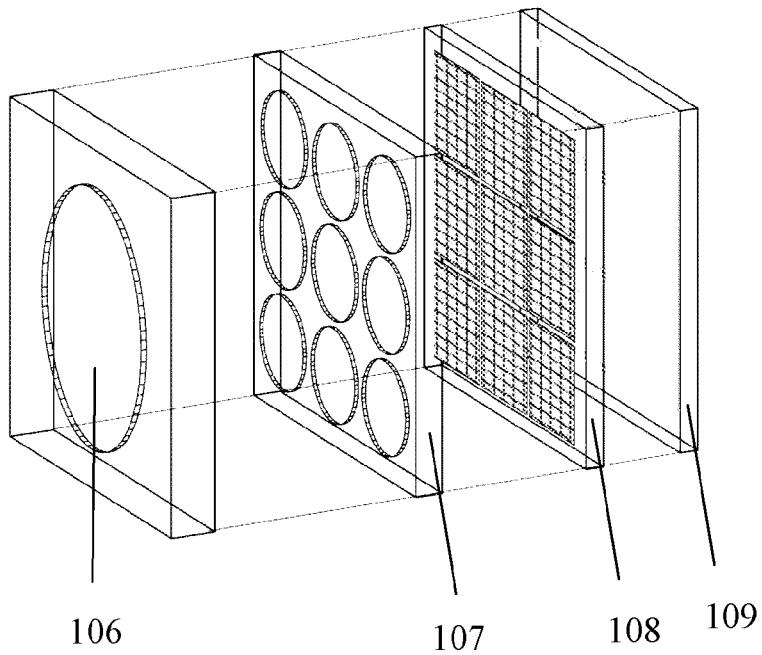
FIG. 2 is a structurally schematic view of a light field imaging module of the present invention.

As shown in FIG. 2, the light field imaging module is adopted to achieve the light field camera function in this embodiment.

The light field imaging module, adapted for achieving light field imaging of the object to be tested, sequentially comprises a convergent lens 106, a microlens array 107, a detector 108 and a first control circuit 109 along a light entrance direction, wherein: the convergent lens converges lights from the filter array on a plane of microlenses of the microlens array, the microlens array projects lights from the filters corresponding to the microlenses on the detector in a form of spectrums, the detector detects the spectrums or light field imaging results of the object to be tested, the first control circuit controls the detector to shoot the spectrums and the light field imaging results.

The detector is able to be any one of existing detectors, such as CCD or CMOS.

The microlenses of the microlens array are respectively corresponding to the filters of the filter array; the projection of each microlens on the filter array is completely located in an area covered by a single filter corresponding to the microlens; the microlens array is located on a focal plane of the convergent lens; the detector is located on a focal plane of the microlens array; a focal length of each microlens is the same. A gap $\delta$ is provided between adjacent microlenses of the microlens array and is coated with a light-absorbing film made from metal chromium, a relationship between the gap $\delta$ and a diameter $\sigma$ of defocused spots of the focal plane of each microlens of the microlens array is $\delta \geq \sigma$. The light-absorbing film, which is coated on the gap between the adjacent microlenses, is able to reflect a part of stray lights for reducing light interferences between the adjacent microlenses.

The lights sequentially pass through the convergent lens 106 and the microlens array 107 and then converge on a plane of the detector 108, and the first control circuit 109 controls the detector 108 to convert optical signals into electrical signals.

External lights from different locations and a certain direction converge on a corresponding microlens of the microlens array 107 which is located at the focal plane of the convergent lens through the convergent lens 106 which comprises multiple sub-lenses. The microlens array is able to be a planar array and a linear array, such as a 1×12 linear array, or 2×6 planar array, or 3×4 planar array each of which comprises 12 microlenses.

In order to reduce aberrations, each microlens of the microlens array is a plano-convex aspherical lens, a plano side of each microlens faces towards the convergent lens 106, a convex side faces towards the detector 108. In many embodiments, each gap is coated with a light absorbing or reflecting film.

The convergent lens is placed at a forefront of the light field imaging module and is at least one member selected from a group consisting of plano-convex lens, biconvex lens and aspherical lens.

An interlayer support structure is located between the microlens array 107 and the detector 108, and a length of the interlayer support structure is equal to the focal length of the microlens array. The interlayer support structure is adapted for securing optical paths.

The above-described embodiments merely illustrate the principles and effects of the present invention and are not intended to limit the present invention. Any person skilled in the art will be able to modify or alter the above-described embodiments without departing from the spirit and scope of the present invention. Accordingly, all equivalents or modifications that may be made by those skilled in the art without departing from the spirit and technical concept disclosed in the present invention are intended to be embraced by the claims of the present invention.

What is claimed is:

1. A light splitting module for obtaining spectrums of an object to be tested, sequentially comprising a light entrance window, a diffuser and a filter array along a light entrance direction, wherein: a size of the filter array is Dx×Dy, maximum divergent angles of the diffuser along a horizontal direction and a vertical direction thereof are respectively $\theta_x$ and $\theta_y$, a distance d between the filter array and the diffuser meets $$0 < d \leq \min\left\{\frac{D_x}{2}\cot\theta_x, \frac{D_y}{2}\cot\theta_y\right\},$$

the light entrance window is made from materials which is transparent at specific bands, the specific bands are target bands of the light splitting module, the filter array is an angle modulated filter array which has multiple subareas and comprises multiple filters with different center wavelengths respectively corresponding to the subareas, a maximum divergent angle of the diffuser is $\theta_{max}=\max\{\theta_x, \theta_y\}$, and a maximum adjustable angle α of the filters of the filter array meets $\alpha \leq \theta_{max}$.

2. A dual-mode multiplexing optical device, comprising:
a light splitting module for obtaining spectrums of an object to be tested, which sequentially comprises a light entrance window, a diffuser and a filter array along a light entrance direction, wherein a size of the filter array is Dx×Dy, maximum divergent angles of the diffuser along a horizontal direction and a vertical direction thereof are respectively $\theta_x$ and $\theta_y$, a distance d between the filter array and the diffuser meets $$0 < d \leq \min\left\{\frac{D_x}{2}\cot\theta_x, \frac{D_y}{2}\cot\theta_y\right\},$$

the light entrance window is made from materials which is transparent at specific bands, the specific bands are target bands of the light splitting module, the filter array is an angle modulated filter array which has multiple subareas and comprises multiple filters with different center wavelengths respectively corresponding to the subareas, a maximum divergent angle of the diffuser is $\theta_{max}=\max\{\theta_x, \theta_y\}$, and a maximum adjustable angle α of the filters of the filter array meets $\alpha \leq \theta_{max}$;
an illumination module adapted for providing the object to be tested with illumination; and
a light field imaging module adapted for achieving light field imaging of the object to be tested, which sequentially comprises a convergent lens, a microlens array, a detector and a first control circuit along the light entrance direction, wherein: the convergent lens converges lights from the filter array on a plane of microlenses of the microlens array, the microlens array projects lights from the filters corresponding to the microlenses on the detector in a form of spectrums, the detector detects the spectrums or light field imaging results of the object to be tested, the first control circuit controls the detector to shoot the spectrums and the light field imaging results,
wherein: the illumination module and the light splitting module form a whole, the illumination module is placed at one side of the light entrance window of the light splitting module, the light splitting module is in detachable connection with the light field imaging module.

3. The dual-mode multiplexing optical device, as recited in claim 2, wherein a surface of the diffuser is coated with a layer of antireflective film, and/or the surface of the diffuser has a surface profile in a form of the microlens array.

4. The dual-mode multiplexing optical device, as recited in claim 2, wherein the filters of the filter array are Fabry-Perot filters, film filters or interference filters.

5. The dual-mode multiplexing optical device, as recited in claim 2, wherein the illumination module further comprises a second control circuit for controlling lightening the illumination module and adjusting brightness of the illumination module.

6. The dual-mode multiplexing optical device, as recited in claim 2, wherein the microlenses of the microlens array are respectively corresponding to the filters of the filter array; a projection of each microlens on the filter array is completely located in an area covered by a single filter corresponding to the microlens; the microlens array is located on a focal plane of the convergent lens; the detector is located on a focal plane of the microlens array; a focal length of each microlens is the same; a gap δ is provided between adjacent microlenses of the microlens array and is coated with a light-absorbing film, a relationship between the gap δ and a diameter σ of defocused spots of the focal plane of the microlens array is δ≥σ; the light-absorbing film is adapted for reducing light interferences between the adjacent microlenses.

7. The dual-mode multiplexing optical device, as recited in claim 6, wherein every filter is square, a diameter of every microlens of the microlens array is smaller than or equal to an inscribed circle diameter of the square filter.

8. The dual-mode multiplexing optical device, as recited in claim 2, wherein all microlenses are aspherical.

9. The dual-mode multiplexing optical device, as recited in claim 2, wherein the convergent lens is placed at a forefront of the light field imaging module and is at least one member selected from a group consisting of plano-convex lens, biconvex lens and aspherical lens.

10. The dual-mode multiplexing optical device, as recited in claim 2, wherein an interlayer support structure is located between the microlens array and the detector, and a length of the interlayer support structure is equal to a focal length of the microlens array.

* * * * *